United States Patent [19]
Ross et al.

[11] Patent Number: 4,619,275
[45] Date of Patent: Oct. 28, 1986

[54] GROUNDING RING

[75] Inventors: Danny E. Ross, Plantation; Larry O. Bond, Davie, both of Fla.

[73] Assignee: Motorola, Inc., Schaumburg, Ill.

[21] Appl. No.: 762,468

[22] Filed: Aug. 5, 1985

[51] Int. Cl.⁴ ............................................. A61N 1/14
[52] U.S. Cl. .................................... 128/783; 361/212; 361/220; 339/14 R
[58] Field of Search .................. 174/5 SG, 6; 339/11, 339/14 R, 147 P; 361/212, 220; 128/783

[56] References Cited
U.S. PATENT DOCUMENTS 3,128,138  3/1960  Noschese .......................... 339/14 R
4,104,695  8/1978  Hollis et al. ......................... 361/220
4,373,175  2/1983  Mykkanen ........................... 361/212
4,402,560 10/1983  Swainback .......................... 339/14 R Primary Examiner—Kyle L. Howell
Assistant Examiner—Randy Citrin
Attorney, Agent, or Firm—Martin J. McKinley; Joseph T. Downey; Donald B. Southard

[57] ABSTRACT

Apparatus for discharging accumulated electrostatic charge from the human body includes a conductive ring to be worn on a finger. A first connector is attached to and electrically connected to the conductive ring. A cable with a mating connector plugs into the first connector. A second connector at the other end of the cable is connected to ground. A series resistor, located in the mating connector housing, limits current flow to a safe level in the event the user comes into contact with a high voltage high current source.

1 Claim, 2 Drawing Figures

GROUNDING RING

BACKGROUND OF THE INVENTION

This invention relates to an apparatus for electrically contacting the human body and more particularly to grounding devices that inhibit electro-static discharge from the human body.

Semiconductor devices constructed from metal oxide semiconductor field effect transistors ("MOS FET") are easily damaged by electro-static discharge. Examples of two well known semiconductor technologies that utilize MOSFET transistors are the "N" channel MOS ("NMOS") technology and the complimentary MOS ("CMOS") technology.

Each of the transistors that make up the semiconductor chip include an "N" or "P" type channel, a thin insulating oxide layer over the channel, and a conductive gate of metal or silicon over the insulating layer. One end of the channel is referred to as the "source" and the other end as the "drain". If a high voltage, such as is present in an electro-static discharge, comes into contact with the gate of the transistor, the thin oxide layer breaks down and current flows into the gate resulting in permanent damage to the transistor.

To make the transistors less susceptible to damage by electro-static discharge, a pair of diodes are normally used on each transistor to clamp the gate voltage between set limits. In particular, the anode of a first diode is connected to the transistor's gate and the cathode is connected to the integrated circuit's positive power supply terminal, while the cathode of a second diode is connected to the gate and the anode is connected to the I.C.'s negative power supply terminal. If a high voltage from an electro-static charge comes into contact with the gate causing the gate voltage to exceed the positive supply voltage, the first diode conducts and dissipates the electro-static charge. Similarly, if the gate voltage goes below the negative supply voltage, the second diode conducts and dissipates the electro-static charge. Although the diodes reduce the number of semiconductor chips that are destroyed, they do not completely eliminate electro-static discharge damage.

The major cause of electro-static discharge damage is the build up of electro-static charge on the human body and its subsequent discharge through the semiconductor during handling. Some clothing materials worn by those handling the semiconductors and the materials covering the floors that they walk on increase the amount of electro-static charge accumulated on the body, thereby increasing the potential for damage. Low relative humidity also compounds the problem, and voltage potentials on an electro-statically charged human body have been measured in the range of 4 to 15 Kilo-Volts.

To reduce or eliminate this accumulated electro-static charge on the human body, persons handling electro-static sensitive semiconductors usually wear a grounded wrist strap. Two types are commonly used. The first type is an elastic wrist strap which incorporates a non-conductive elastic band with a conductive foil attached to the inside of the elastic band. The elastic strap is intended to be worn on the wrist with the foil contacting the upper side of the wrist. The foil is secured to the elastic band with a rivoted snap and a grounding cable with a mating snap attaches to the foil at the rivoted snap.

There are several problems with the elastic strap. One problem is that permanent stretching and loss of elasticity occurs with use and the elastic band fails to hold the conductive foil against the wrist. Another problem occurs if the user wears the elastic strap with the conductive foil on the underside of the wrist. Worn in this fashion, the cable has a tendency to pull the foil away from the skin. When the elastic strap is worn with the foil on top of the wrist, however, the amount of hair that normally grows in that area of the wrist often prevents good electrical contact between the foil and the skin. In addition, the snap type connectors often become intermittant.

The second type of wrist strap is the metal wrist strap which incorporates a stretchable and conductive metal band, such as the type commonly used with wrist watches. A metal snap is attached to the metal band and a grounding cable with a mating snap attaches to the metal band at the snap. The metal band can be uncomfortable to wear because it often pinches the skin or pulls the hair of the wearer. When new, the band is sized to provide good electrical contact when worn on a small wrist. Consequently, blood circulation is somewhat restricted and discomfort occurs when the band is worn for an extended time on a larger wrist. When the band is alternately worn on different size wrists, as often occurs do to changes of personnel during different factory shifts, permanent stretching occurs with use and good electrical contact is no longer provided to a small wrist. As with the elastic strap, the snap type connector often becomes intermittant.

SUMMARY OF THE INVENTION

Accordingly, an object of the invention is to provide an improved apparatus for electrically contacting the human body.

Another object of the invention is to provide an improved apparatus for removing electro-static charge from the human body.

Another object of the invention is to provide an apparatus for electrically contacting the human body at a more suitable location than the wrist.

Another object of the invention is to provide a body electrical contacting apparatus that will not permanently stretch out of shape with use.

Another object of the invention is to provide a body electrical contacting apparatus that will not pinch the skin, pull the hair, or restrict the blood circulation of the user.

Another object of the invention is to provide a body grounding apparatus that has a reliable electrical connector between the body contacting apparatus and the grounding cable.

Another object of the invention is to provide a body grounding apparatus having a connector with a current limiting resistor built into the connector.

Still another object of the invention is to provide a body electrical contacting apparatus that is small in size and inexpensive to manufacture.

Briefly, the invention includes and electrically conductive finger ring, engagable with a finger, for electrically contacting the finger. A connector is attached to and electrically connected to the conductive finger ring.

In an alternate embodiment, the invention includes an electrically conductive finger ring, engagable with a finger, for electrically contacting the finger. An electrical cable is attached to and electrically connected to the conductive finger ring.

In still another embodiment, the invention includes an electrically conductive finger ring, engagable with a finger, for electrically contacting the finger. An electrically conductive connector ring with an aperture is attached to and electrically connected to the conductive finger ring. A connector plug, for insertion into the connector ring, has a substantially longitudinal slot and a retaining flange. An attaching flange is connected to the connector plug. A housing has a cavity with an internal groove into which the attaching flange is inserted. The housing includes two complimentary parts both having an external groove into which a snap ring is inserted to join the complimentary parts together. A resistor is located in the cavity and electrically connected to the connector plug.

DESCRIPTION OF THE PREFERRED EMBODIMENT

Figure 1:
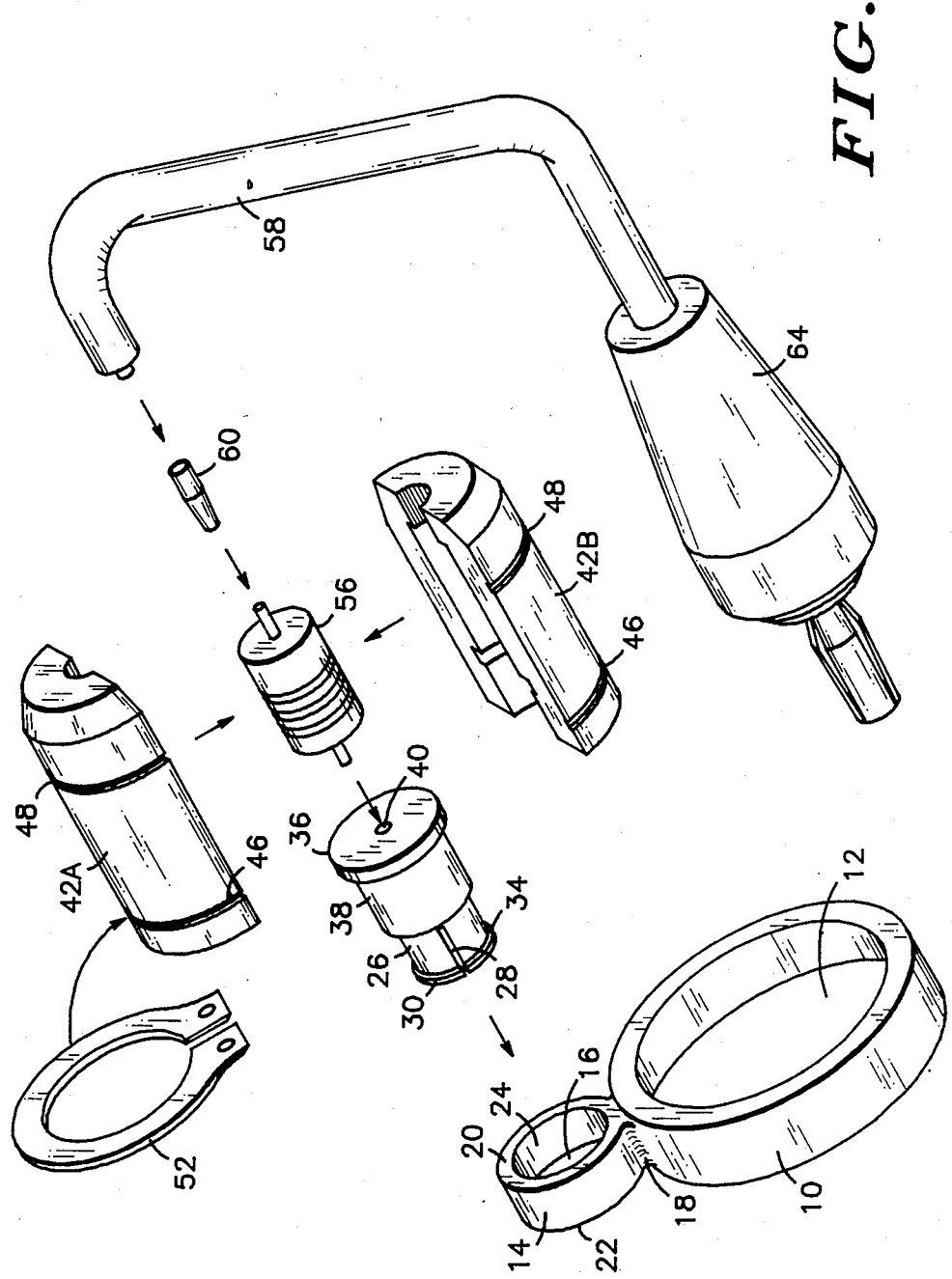
FIG. 1 is a perspective drawing of the preferred embodiment showing an exploded view of the connector at the ring end of the cable.

Referring now to FIG's 1 and 2, a finger ring 10, having an aperture 12, is sized to be worn on a finger of the human hand. Finger ring 10 is preferable constructed from brass and plated with nickel. Although brass is the preferred material, any material known in the art that can be plated or otherwise coated with any other known conductive material should be suitable. The wall thickness of the finger ring 10 is preferably a minimum of 0.115 inches, and the width of the ring is preferably 0.256 inches.

A connector ring 14 having an aperture 16 is preferably welded to finger ring 10 at weld 18, thereby providing both physical attachment and electrical connection to the finger ring. Connector ring 14 has edges 20 and 22 and an interior surface 24. Connector ring 14 is preferably constructed from the same materials as finger ring 10. The width of connector ring 14 is preferably 0.168 inches, the wall thickness is preferably 0.115 inches, and the diameter of aperture 16 is preferably 0.140 inches.

A connector plug 26 having a longitudinal slot 28 can be inserted into aperture 16 of connector ring 14 to provide both physical attachment and electrical connection to finger ring 10. Upon insertion into aperture 16, longitudinal slot 28 permits connector plug 26 to compress slightly, thereby maintaining good physical and electrical contact with interior surface 24 of connector ring 14.

Figure 2:
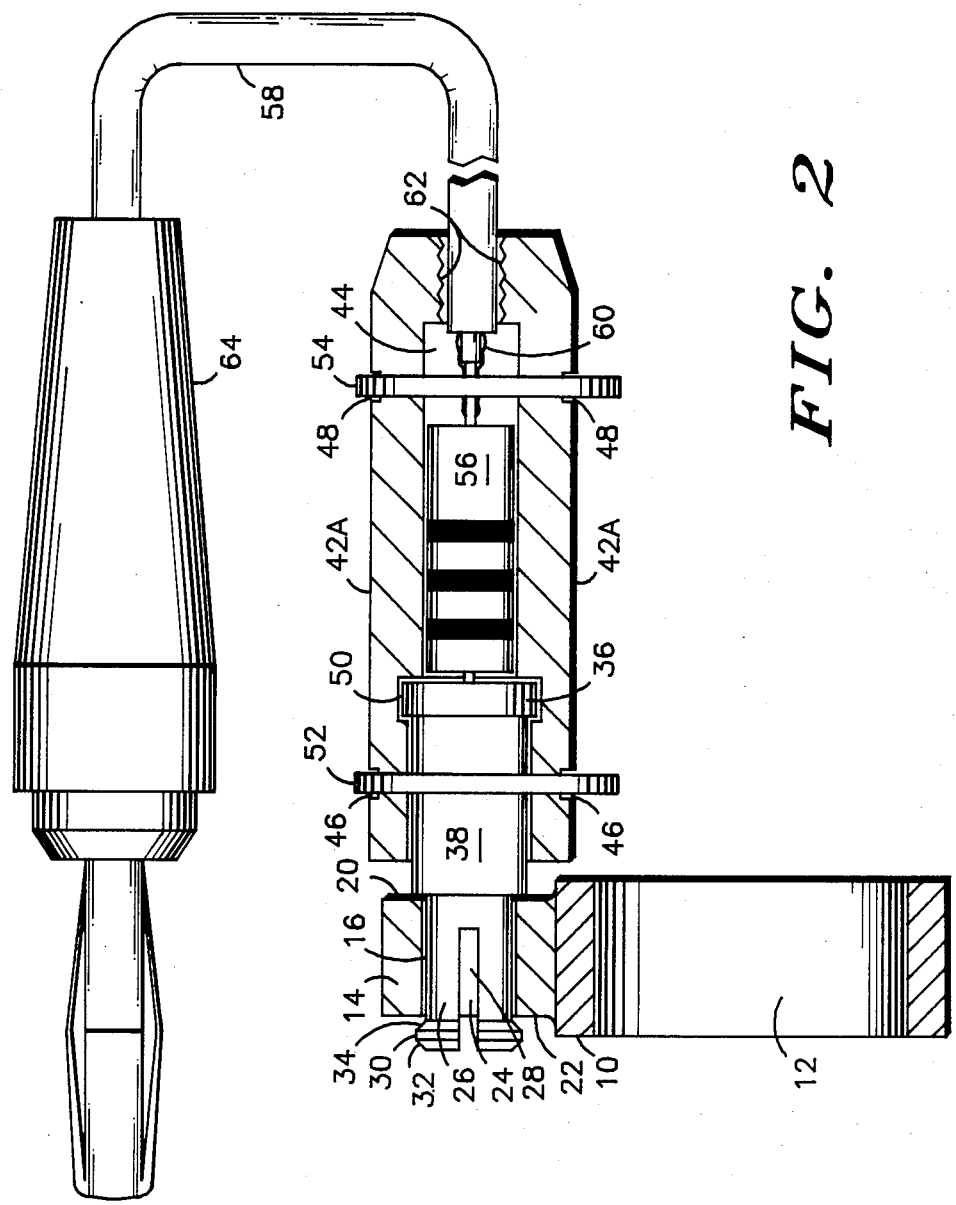
FIG. 2 is a side view of the preferred embodiment with one of the two connector complimentary housing shells removed. The finger ring and the ring connector are shown sectioned on a plane coincident with the center axes of both the finger ring and the connector ring.

A retaining flange 30 with beveled edges 32 and 34 (FIG. 2) is located at the tip of connector plug 26. Retaining flange 30 is slightly larger than the diameter of connector plug 26, so that as the connector plug is being inserted into aperture 16 of connector ring 14, interior wall 24 compresses the connector plug until the retaining flange slides completely through aperture 16. After retaining flange 30 is completely through aperture 16, connector plug 26 expands slightly and the retaining flange butts against surface 22 of connector ring 14, thereby retaining the connector plug in the aperture until sufficient force is applied to recompress the connector plug and remove it from the connector ring. Beveled edges 32 and 34 assist in starting the compression process when connector plug 26 is being respectively inserted into or removed from connector ring 14.

An attaching flange 36 is connected to connector plug 26 through body 38. Attaching flange 36 has a soldering hole 40. Attaching flange 36, body 38, connector plug 26, and retaining flange 30 along with beveled edges 32 and 34, are all preferably machined from Beryllium Copper, Nickel plated, and heat treated for 2 hours at 600° C.

A housing 42 comprised of two identical and complimentary shells 42a and 42b has a cavity 44, two external grooves 46 and 48, and one internal groove 50. Housing 42 is preferable constructed from Polytetrafluoroethylene, although other insulating materials known in the art are suitable. Attaching flange 36 is inserted into internal groove 50 to attach housing 42 to connector plug 26. Complimentary housing shells 42a and 42b are fastened together by inserting well known snap rings 52 and 54 respectively into external grooves 46 and 48.

A resistor 56 has one lead preferably soldered into hole 40 of attaching flange 36 and the other lead soldered to cable 58. Resistor 56 has a preferred value of 1 Meg-Ohm but any large value of resistance is suitable. Resistor 56 functions as a current limiting resistor to prevent serious electrical shock to the person wearing the invention in the event that he or she accidentally comes into contact with a high voltage source that is capable of sourcing a lethal current through the human body. A small piece of well known heat shrink tubing 60 covers the soldered connection of cable 58 and resistor 56. Small circular grooves 62 in housing 42 grasp cable 58 providing strain relief. The other end of cable 58 has a connector 64, preferable a well known banana plug, although any type of connector well known in the art is suitable.

When the invention is used to discharged accumulated electro-static charge from the body, connector 64 is connected to ground. Although the preferred use for the present invention is as a device to ground the human body to prevent the build up of electro-static charge, its use could also include other applications. For example, the present invention could be used in medical applications as a device to provide interconnection between an electronic medical instrument and the human body.

Although, the size of the preferred embodiment of finger ring 10 is not adjustable, size adjustment can easily be provided. For example, a gap can be cut in the wall of finger ring 10 and the diameter of the ring varied by either closing the gap to make the size smaller or opening the gap to make the ring size larger.

If so desired, connector ring 14 and its mating plug can be eliminated and cable 58 electrically connected directly to finger ring 10. Resistor 56 can then be encorporated directly into cable 58, as by encapsulation.

We claim:
1. Apparatus for electrically contacting the human body at a finger, comprising in combination:
   an electrically conductive finger ring, engagable with said finger, for electrically contacting said finger;
   an electrically conductive connector ring having an aperture, said connector ring being electrically connected to said conductive finger ring and attached to the outside of said conductive finger ring;

an electrical connector plug, removably inserted into said connector ring, said connector plug having a substantially longitudinal slot and a retaining flange;

an attaching flange attached to said connector plug;

a housing having a cavity, said cavity having an internal groove, said attaching flange being inserted into said internal groove;

said housing including two complementary parts, said parts having an external groove;

a snap ring, inserted into said external groove, to join said complementary parts; and a resistor, located in said cavity and electrically connected to said connector plug.

* * * * *